United States Patent [19]

Yu

[11] Patent Number: 4,774,943
[45] Date of Patent: Oct. 4, 1988

[54] ENDOTRACHEAL TUBE

[76] Inventor: Charles C. Yu, 4920 Hogans Lake Pl., Annandale, Va. 22003

[21] Appl. No.: 948,052

[22] Filed: Dec. 31, 1986

[51] Int. Cl.⁴ .................... A61M 16/00; A62B 9/06
[52] U.S. Cl. .................. 128/207.14; 128/DIG. 26; 128/207.17; 604/179
[58] Field of Search ............... 128/200.26, 207.14, 128/207.15, 207.16, 207.17, 207.18, 911, 912, DIG. 26; 604/264, 117, 174, 179

[56] References Cited

U.S. PATENT DOCUMENTS

| | | | |
|---|---|---|---|
| 2,765,792 | 10/1956 | Nichols | 128/200.26 |
| 2,786,469 | 3/1957 | Cohen | 128/200.26 |
| 2,820,457 | 1/1958 | Phillips | 128/200.26 |
| 3,088,466 | 5/1963 | Nichols | 128/200.26 |
| 3,480,003 | 11/1969 | Crites | 128/734 |
| 4,232,665 | 11/1980 | Vaseen | 128/200.24 |
| 4,261,363 | 4/1981 | Russo | 128/200.26 |
| 4,270,529 | 6/1981 | Muto | 128/DIG. 26 |
| 4,296,949 | 10/1981 | Muetterties et al. | 285/18 |
| 4,332,242 | 6/1982 | Chikama | 128/3 |
| 4,340,046 | 7/1982 | Cox | 128/207.14 |
| 4,452,473 | 6/1984 | Ruschike | 604/283 |
| 4,607,868 | 8/1986 | Harvey et al. | 604/241 |

OTHER PUBLICATIONS

ACMI Catheters and Accessories, Feb. 1961, American Cystoscope Makers, Inc., 8 Pelham Parkway, Pelham Manor, New York.

Primary Examiner—Francis J. Jaworski
Assistant Examiner—George Manuel
Attorney, Agent, or Firm—Parkhurst, Oliff & Berridge

[57] ABSTRACT

An improved endotracheal tube is disclosed which provides for a more reliable and safer airway to a patient's lungs for the purpose of administering anesthesia, supplying oxygen and assisting a patient in breathing, and the like. The new and improved features of the tube make it easier for a health care professional to secure the tube to a patient's face, monitor its depth of insertion into the throat and assure its easy connection an disconnection from a medical or surgical apparatus. These improved features include flexible flanges molded to the tube, each of said flanges including a plurality of radially opposite slots to which adhesive tape is attached for securing said tube to a patient's face. The tube is also provided with colored rings, located between the upper and lower edges of each set of slots for monitoring the depth of insertion of the tube into the throat of a patient. A connection end of the tube is fitted with internal threads for threadedly engaging a universal connector for attachment to a medical or surgical apparatus.

14 Claims, 1 Drawing Sheet

ENDOTRACHEAL TUBE

BACKGROUND OF THE INVENTION

This invention relates to endotracheal tubes which are well known in the medical and surgical fields for their use in administering oxygen or anesthesia to a patient and for maintaining an airway to a patient's lungs. More particularly, this invention relates to devices for securing such tubes to a patient's face, monitoring the depth of insertion of the tubes and providing for easy connection and disconnection to medical and surgical devices.

Exemplary devices for securing a tube to a patient's face are disclosed in U.S. Pat. No. 4,270,529 to Muto, wherein a faceplate is held in position by strands located around the head, said faceplate including a slot for sliding a mouthpiece in position to hold the tube. U.S. Pat. No. 2,820,457 to Phillips discloses a positioning retainer which includes a rotatable body member which engages a mouthpiece for compressing a tube and holding it in position.

These known devices are not practical to use. They include many parts that have to be assembled which can take excessive time in critical situations, and they also burden the health care professional with the problem of checking all these parts and connections which distracts attention away from the problem at hand; namely, caring for a patient during an emergency or during intensive care. Moreover, in Muto, some disadvantages are associated with the faceplate. The faceplate extends around the ear in which case the edge of said faceplate could cause injury to the outside of the ear. Also the positioning and removing of the strands requires that the head of the patient be tilted forward causing discomfort to the patient, especially with the tube lodged in the throat.

A more conventional method for securing a tube to a patient's face involves wrapping tape around the outside of the tube and onto the face of the patient. This method is undesirable because the tape does not remain in place due to wetness from the patient's saliva, sweat from the skin of the patient or for other reasons. Therefore, the tube can slide up and down within the trachea of the patient. Such sliding of the tube can have critical ramifications. For example, if the tube slides too far down into the lungs, only one half of the lungs may be supplied with oxygen or anesthesia, and the other half of the lungs may collapse. If the tube is located too high up in the throat, its intended functions also cannot be achieved. The presence of the tape on the tube causes another problem, specifically, the tape covers up numbers located on the outside of insertion of the tube, said numbers indicating the depth of the tube into a patient's throat. Moreover, the numbers, even when not covered by the tape, are difficult to read from a distance because of their small size. Still further, nurses, technicians or orderlies involved with checking the depth of the tube do not always understand the meaning of the numbers and accordingly, have difficulty in determining if the tube is inserted a proper depth into the patient's throat.

A still further disadvantage associated with these and other tubes relates to attaching the tubes to medical and surgical devices. Particularly, tubes are fitted at their connection end with a universal connector. The universal connector is lodged inside the tube and is held in place by a frictional pressure exerted on its outer surface by the inside walls of the tube.

Normally, the connection end of the endotracheal tube, which engages the universal connector, has a diameter which is larger than the diameter of the remainder of the tube to permit insertion of the universal connector into the tube. A major problem arises when the connection end of the tube is cut to conform to a required length. For example, if the endotracheal tube is inserted into a patient having a trachea, such as an infant, the tube sticks out of the mouth of the patient much too far, thereby requiring the connection portion of the tube to be cut to shorten the tube. Thus, if the large diameter portion of the tube located at the connection portion of the tube is removed by cutting, a much larger force will be required to insert the universal connector into the smaller diameter portion of the tube. Particularly, the tube will have to be stretched in a radial direction to accommodate the universal connector. Consequently, it is even more difficult to insert and dislodge the connector because of the stronger frictional pressure exerted on the connector by the inside portion of the endotracheal tube walls. The additional force required to insert and dislodge the universal connector is undesirable because such force can result in accidentally pushing the tube too far into the treachea of the patient or pulling the tube too far out of the trachea of the patient.

SUMMARY OF THE INVENTION

The present invention was made in view of the foregoing background and to overcome the foregoing drawbacks. Particularly, the present invention relates to an improved endotracheal tube which includes at least one flexible flange integrally molded to the tube or securely fixed to the tube. The flanges comprise at least one pair of slots located on radially opposite sides of the tube to which adhesive tape can be attached for securing the tube to the face of a patient. After determining the required length of tube which is to be inserted into the trachea of a patient, adhesive tape is attached around a longitudinally extending portion of each of a pair of flanges which form said slots. Any remaining excess flanges which form slots which are not connected with the tape could be cut away from the tube, if desired. However, if the excess flanges do not result in any inconvenience, they could remain attached to the tube. The tape used to secure the tube to the face of a patent is also novel. Particularly, the tape has one sticky side which is covered by a pectable coating. Also, the tape has two axial extending portions which assist in peeling the coating away from the tape, and also assist in securing the tape to the flanges of the tube. The improved method of attaching the tape will prevent it from sliding along the outer surface of the tube, as is the case with presently used methods.

Moreover, to overcome the problem of determining an accurate depth of insertion of the tube into the trachea of a patient, colored rings are provided on an outer surface of the tube. The colored rings are positioned on the outer surface of the tube such that they are between adjacent radially extending portions of the flanges on the tube. These colored rings can be seen from a distance and they present an easy reference for monitoring the depth of insertion of a tube. Another advantage of these rings is that if a tube is removed or dislodged from a patient's throat, the rings provide an easy reference as to what depth the tube is to be reinserted. No disconnections or reconnection of any parts are required and no readjustment of any faceplate or mouthpiece is necessary.

Another feature of the present invention is that the tube is fitted at its connection end with internal threads for threadedly engaging external threads of a universal connector.

It is another object of the present invention to provide an improved endotracheal tube which is made of one piece or one integral part, in contrast to the prior art wherein the tube has associated with it many different and separate parts.

BRIEF DESCRIPTION OF THE DRAWINGS

The above objects, features and advantages of the present invention will become more apparent from the following description of the preferred embodiments taken in conjunction with the accompanying drawings, wherein.

DETAILED DESCRIPTION OF THE INVENTION

Figure 1:
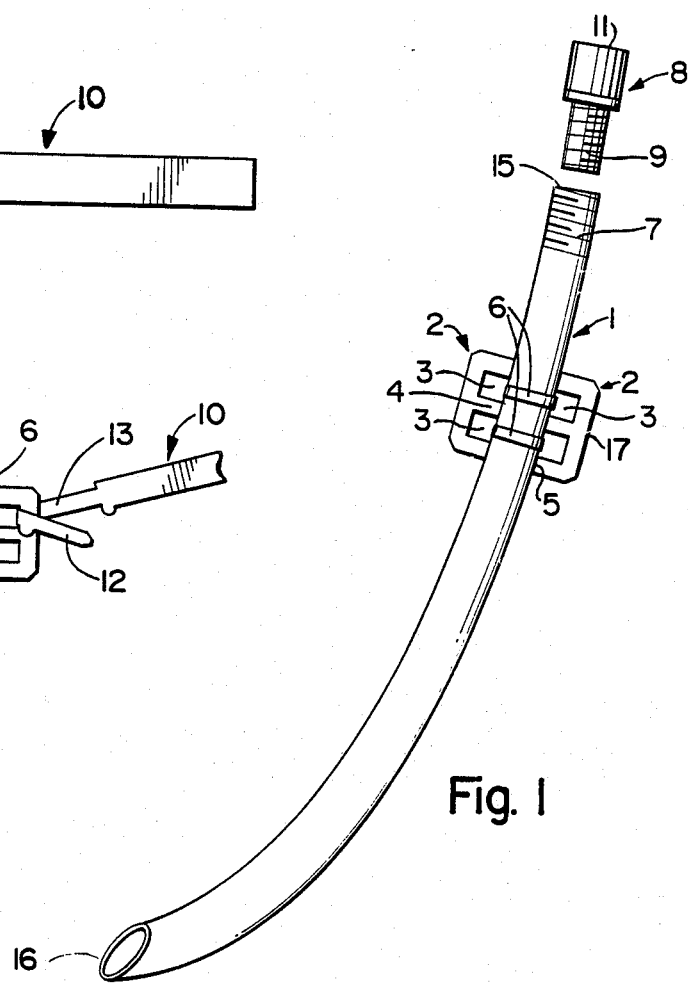
FIG. 1 is a perspective view of the endotracheal tube according to the present invention.

An improved endotracheal tube 1 is constructed as an integral assembly, as shown in FIG. 1. A plurality of flanges 2 extend radially outward from an outer surface of the tube. The plurality of flanges 2 are fixed to the tube 1 by an appropriate method, or the plurality of flanges 2 can be integrally molded with the tube 1. The plurality of flanges 2 are typically located closer to a connection end portion 15 of the tube than an insertion end portion 16 of the tube. The primary criteria for determining the precise location of the flanges 2 are the typical lengths of tracheas into which the endotracheal tubes are to be inserted. The plurality of flanges are provided on the outer surface of the endotracheal tube 1 such that the flanges located closest to the insertion end 16 of the endotracheal tube 1 would be utilized for short tracheas, whereas the flanges 2 located closest to the connection end portion 15 of the tube 1 will be utilized for long tracheas. The flanges 2 are made of a flexible material, preferably made out of the same material as that of the tube 1 itself. Each flange includes a plurality of openings 3 which are defined by at least two radially extending portions 4 and at least one longitudinally extending portion 17 which connects said at least two radially extending portions 4. The openings 3 are located at different locations along the length of the tubular body portion of the device.

The flanges are utilized as follows: once the appropriate insertion depth of the endotracheal tube into the trachea of a patient has been determined, the determination of which pair of slots 3 which are to be utilized for securing the tube to the face of a patient can also be determined. Thus, if the pair of slots 3 closest to the connection end portion 15 of the tube 1 is determined to be the appropriate pair of slots to be utilized, then all other portions 17 and 4 may be cut away from the tube 1 to permit complete insertion of the tube into the trachea of a patient.

Moreover, if the pair of slots 3 located closer to the insertion end portion 16 of the tube 1 is determined to be the appropriate slots to be utilized, then the remainder of the slots 3 can be removed by cutting them away from the tube along the portions 4 and 17. However, it may not be necessary to remove such slots unless they inconvenience access to the patient or hinder adhering the tube to the face of the patient.

Figure 3:
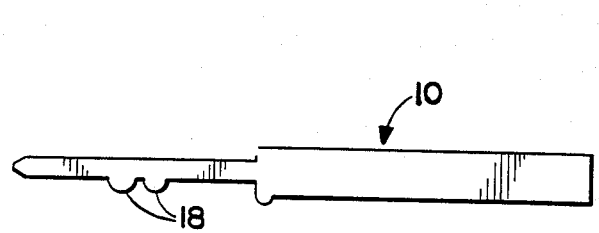
FIG. 3 shows a more detailed view of the tape used to secure the tube to the face of the patient.
Figure 2:
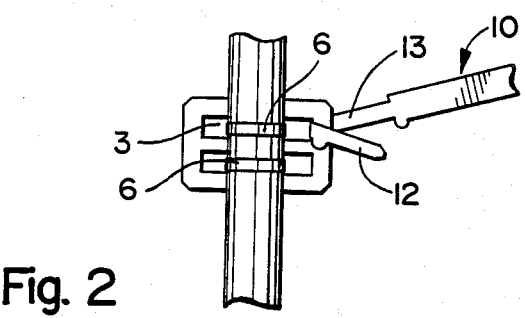
FIG. 2 shows the method of securing tape to a slot in a flange of the tube.
Figure 4:
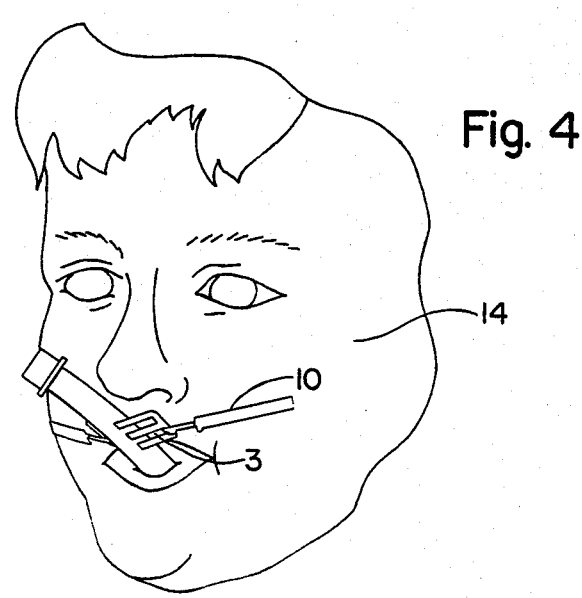
FIG. 4 shows a more detailed view of the tape used to secure the tube to the face of the patient.

FIGS. 2 and 4 of the application show in detail how the slots 3 are utilized in combination with an adhesive tape 10 for securing the endotracheal tube to the face of the patient. For example, FIG. 2 shows an endotracheal tube wherein two pairs of slots 3 located on radially opposite sides of the tube remain. An adhesive tape 10, shown in detail in FIG. 3, is wrapped around a longitudinally extending portion 17 of the slots 3. The tape which is utilized to secure the tube to the patient's face is also novel in that only one side of it has adhesive portions, as identified by the numerals 12 and 13 in FIG. 2. This one sticky side of the tape is exposed by peeling a covering away from the tape and thereafter combining the sticky portions appropriately. The tape 10 includes at least two axially extending portions 18 which assist in the removal of the covering from the tape. Also, the axially extending portion 18 assist in sealing the tape to the flanges 3, as shown in FIG. 2. Specifically, one of the axially extending portions 18 is located on a first side of the longitudinally extending portion 17 and a second of the axially extending portions 18 is located on a second side of the longitudinally extending portion 17.

The precise manner for affixing the tube to the face of the patient is as follows. Once the appropriate pair of slots 3 have been determined, the tape 10 is inserted into the slot 3 and around the longitudinally extending portion 17. Sticky portions of the tape 10 are then exposed by peeling away the covering and the sticky portions 12 and 13 of the tape are then contacted together. As shown in FIG. 4, the tape is then secured to appropriate portions on the face of the patient 14. This novel combination of utilizing the flanges 2, which include the slots 3, along with the tape 10, provides for a novel manner of affixing an endotracheal tube to the face of the patient.

A further embodiment of the invention is the including of depth indicating rings 6 on an outer surface of the endotracheal tube 1. The depth indicating rings are preferably colored rings 6 of different colors. The rings 6 utilized to identify a proper insertion depth of the endotracheal tube into the trachea of a patient. A typical location for the rings 6 is between the radially extending portion 4 of the flanges 2. The colored rings are intended to substitute for the previously utilized numbers which historically have been printed on the outside portion of an endotracheal tube 1. For example, the printed numbers typically correspond to the depth that the insertion end portion 16 of the tube 1 has been inserted into the trachea of a patient. If a tube was inserted into the trachea of a patient and only the number 25 could be viewed sticking out from the mouth of a patient, it could be determined that the tube had been inserted approximately 25 centimeters into the trachea of the patient, as measured from the distance from the number to the insertion end 16 of the endotracheal tube. While such numbers do serve a purpose, they can add confusion to an emergency situation. Many times technicians or nurses in charge of securing an endotracheal tube to a patient either do not know the meaning of the numbers; or even if they do know the meaning of the numbers, do not know how the numbers should be utilized in the particular instance; or cannot read the numbers due to the excessive amounts of tape that are used to secure the endotracheal tube to the face of the patient. However, by providing the colored rings 6 on the outer surface of the endotracheal tube, a much simpler and more reliable method for determining the proper insertion depth of the tube into the trachea of a patient is available.

For example, an orderly or intern who is in charge of checking on an intensive care patient simply needs to glance at a distance at an endotracheal tube and determine if, for example, a green colored ring is showing or a red colored ring is showing, etc. Such observation can be done at a great distance and with minimum effort, as well as with great accuracy. Never before has such a reliable method for the combination of securing the endotracheal tube 1 to the face of a patient been disclosed or suggested or for providing reliable assurance of the insertion depth of the tube into the trachea of a patient.

The tube is also provided at the connection end 15 with a plurality of internal threads 7 which are threaded on an inside portion of the endotracheal tube. These plurality of internal threads 7 should probably extend into the tube at least a distance of 2 inches. The internal threads 7 are present so that they can be combined with external threads 9, located on a universal connector member 8. More specifically, the universal connector member 8 is typically connected to an external respirator or anesthesia gas, or the like, at the portion 11. The external gases are supplied through the universal connector 8 and into the endotracheal tube 1. The disadvantages of the prior art, namely, the frictional engagement of the universal connector 8 to the connection end portion of an endotracheal tube are ameliorated because rather than using a frictional engagement therebetween, the present invention provides for a threaded or screwing engagement between the universal connector 8 and the endotracheal tube 1. The reason that it is necessary for the internal threads 7 to extend at least 2 inches into the endotracheal tube is that if it becomes necessary to cut away a portion of the connection end portion 15 of the endotracheal tube, at least some internal threads 7 will be available for connection with the external threads 9 of the universal connector 8. Thus, all the difficulties associated with the forces which have to be exerted to both insert and extract the previously known universal connectors from an endotracheal tube are ameliorated, because of the simple threading engagement provided.

As can be understood from the above description of the present invention, the invention significantly enhances emergency treatment of a patient who requires use of an endotracheal tube. Never before has the endotracheal tube been so securely attached to the face of the patient; the depth of the tube into the throat of a patient been so easily determined at a distance; and the attachment of the tube to a universal connector been so readily achieved.

While the present invention has been disclosed with a great deal of particularity, the invention should not be narrowly construed and any modifications which would occur to those skilled in the art should be considered to fall within the scope of the claims appended hereto.

What is claimed is:

1. An endotracheal tube comprising:
   a tubular body portion having an inner surface, an outer surface, a length and a longitudinal axis, and said tubular body portion having an insertion end and a connection end; and
   a pair of flange means integral with said tubular body portion, said flange means extending from the exterior of said tubular body portion substantially in a plane which is substantially parallel to the longitudinal axis of the tubular body portion at said flange means, with a plurality of openings in said flange means, said openings being located at different locations along the length of the tubular body portion, for permitting the endotracheal tube to be fixed at a desired depth position within a patient's trachea.

2. The endotracheal tube of claim 1 wherein each of said flanges comprises at least two radially extending portions which are connected by at least one longitudinally extending portion, which is substantially parallel to the axis of the tubular portion, said at least two radially extending portions and said at least one longitudinally extending portion defining one of said pluraity of openings therein.

3. The endotracheal tube of claim 2, wherein at least two radially extending flanges are provided on said body portion, such that each of said flanges is located on a radially opposite side of said body portion.

4. The endotracheal tube of claim 2, wherein at least four flanges are provided on said body portion, such that two flanges are located on each of radially opposite sides of said body portion.

5. The endotracheal tube of claim 2, wherein at least six flanges are provided on said body portion, such that three flanges are located on each of radially opposite sides of said body portion.

6. The endotracheal tube of claim 1, further comprising a plurality of internal threads located within said connection end of the tube.

7. The endotracheal tube of claim 6, further comprising a universal adaptor having a plurality of external threads at a connection end portion thereof, said universal adaptor threadably engaging said internal threads located at said connection end portion.

8. The endotracheal tube of claim 1, additionally comprising a plurality of ring markings around the tubular body portion in the region of the tubular body portion at which said flanges are located, each of said rings being circumferentially marked so as to be immediately visually distinguished from any other immediately adjacent ring.

9. The endotracheal tube of claim 8, wherein the immediately visually distinguishable circumferential markings are rings of different colors, no adjacent two of which are a similar color.

10. The endotracheal tube of claim 1, additionally comprising an adhesive tape member for holding the endotracheal tube at a desired fixed depth position within a patient's trachea, said adhesive tape member having two distinct portions of its length, a first of said length portions passing through an opening in one of said flanges and folded back along its length and securely adhered to its own length, and a second length portion for adhesion to the patient's face to fix the position of the tube within the patient's trachea.

11. The endotracheal tube of claim 10, wherein said first length portion of said adhesive tape member is of relatively narrow widths to facilitate passage thereof through an opening in one of said flanges, and said second length portion of said adhesive tape member is of relatively wide width to enhance adhesion to the patient's face.

12. The endotracheal tube of claim 11, wherein said adhesive tape member further comprises one adhesively sticky side having a removable coating thereon.

13. The endotracheal tube of claim 12, additionally comprising a plurality of ring markings around the tubular body portion in the region of the tubular body portion at which said flanges are located, each of said rings being circumferentially marked so as to be immediately visually distinguished from any other immediately adjacent ring.

14. The endotracheal tube of claim 13, wherein the immediately visually distinguishable circumferential markings are rings of different colors, no adjacent two of which are as similar color.

* * * * *